(12) United States Patent
Shitanda et al.

(10) Patent No.: US 11,996,596 B2
(45) Date of Patent: May 28, 2024

(54) POWER GENERATION DEVICE, POWER GENERATION METHOD, AND CONCENTRATION MEASUREMENT METHOD

(71) Applicants: TOKYO UNIVERSITY OF SCIENCE FOUNDATION, Tokyo (JP); UNIVERSITY OF TSUKUBA, Ibaraki (JP)

(72) Inventors: Isao Shitanda, Tokyo (JP); Seiya Tsujimura, Ibaraki (JP)

(73) Assignees: TOKYO UNIVERSITY OF SCIENCE FOUNDATION, Tokyo (JP); UNIVERSITY OF TSUKUBA, Ibaraki (JP)

( * ) Notice: Subject to any disclaimer, the term of this patent is extended or adjusted under 35 U.S.C. 154(b) by 301 days.

(21) Appl. No.: 16/337,974

(22) PCT Filed: Sep. 28, 2017

(86) PCT No.: PCT/JP2017/035317
§ 371 (c)(1),
(2) Date: Mar. 29, 2019

(87) PCT Pub. No.: WO2018/062419
PCT Pub. Date: Apr. 5, 2018

(65) Prior Publication Data
US 2020/0028195 A1   Jan. 23, 2020

(30) Foreign Application Priority Data
Sep. 30, 2016   (JP) ................ 2016-195054

(51) Int. Cl.
*H01M 8/16*   (2006.01)
*A61B 5/145*   (2006.01)
*G01N 27/416*   (2006.01)

(52) U.S. Cl.
CPC .......... *H01M 8/16* (2013.01); *A61B 5/14532* (2013.01); *G01N 27/416* (2013.01); *A61B 2560/0214* (2013.01)

(58) Field of Classification Search
CPC ........................... H01M 8/16; A61B 5/14532
See application file for complete search history.

(56) References Cited

U.S. PATENT DOCUMENTS 6,403,944 B1 * 6/2002 MacKenzie .......... A61B 5/0095
356/41
2007/0218345 A1   9/2007 Sakai et al.
(Continued)

FOREIGN PATENT DOCUMENTS

JP   2006-024555 A   1/2006
JP   2011-258393 A   12/2011
(Continued)

OTHER PUBLICATIONS

Rappaport et. al; "A Glucose Fuel Cell for Implantable Brain-Machine Interfaces"; Published Jun. 12, 2012 (Year: 2012).*
(Continued)

*Primary Examiner* — Nathanael T Zemui
(74) *Attorney, Agent, or Firm* — MARSHALL, GERSTEIN & BORUN LLP

(57) ABSTRACT

A power generation device, comprising a fuel, an anode and a cathode, the anode comprising an enzyme that promotes oxidation of the fuel, and the power generation device containing more water when generating power than when not generating power.

28 Claims, 4 Drawing Sheets

(56) References Cited

U.S. PATENT DOCUMENTS

| | | | | |
|---|---|---|---|---|
| 2010/0004521 A1* | 1/2010 | Epps | ............ | H01M 8/16 |
| | | | | 600/347 |
| 2013/0065139 A1 | 3/2013 | Nakagawa et al. | | |
| 2013/0253293 A1* | 9/2013 | Ocvirk | ............ | G01N 27/3271 |
| | | | | 600/345 |
| 2014/0287328 A1 | 9/2014 | Samukawa et al. | | |
| 2014/0322617 A1* | 10/2014 | Wang | ............ | H01M 4/8807 |
| | | | | 427/553 |
| 2016/0154256 A1 | 6/2016 | Yajima et al. | | |

FOREIGN PATENT DOCUMENTS

| | | |
|---|---|---|
| JP | 2013-045647 A | 3/2013 |
| JP | 2014-207987 A | 11/2014 |
| WO | WO-2013/065508 A1 | 5/2013 |
| WO | WO-2015/022868 A1 | 2/2015 |

OTHER PUBLICATIONS

Shitanda et al., "Flexible and High-performance Paper-based Biofuel Cells Using Printed Porous Carbon Electrodes", Chem. Comm., 49, 2013, pp. 11110-11112.
Search Report in International Application No. PCT/JP2017/035317 dated Dec. 26, 2017, 4 pages.
Written Opinion ISA in International Application No. PCT/JP2017/035317 dated Dec. 26, 2017, 4 pages.
Written Opinion IPEA in International Application No. PCT/JP2017/035317 dated Jun. 26, 2018, 6 pages.
Preliminary Report on Patentability in International Application No. PCT/JP2017/035317 dated Sep. 10, 2018, 14 pages.
Third Party Opposition filed Jun. 16, 2022, 35 pages.

\* cited by examiner

POWER GENERATION DEVICE, POWER GENERATION METHOD, AND CONCENTRATION MEASUREMENT METHOD

TECHNICAL FIELD

The invention relates to a power generation device, a power generation method, and a concentration measurement method.

BACKGROUND ART

Biofuel cells, which create electricity from biomass resources such as sugars or alcohols, have been studied and developed in recent years.

A biofuel cell generally has electrodes (an anode and a cathode) that are immersed in a liquid containing a fuel, and the anode contains an enzyme that promotes oxidation of the fuel.

Electrons are derived from the anode upon oxidation of the fuel (such as a change of glucose into gluconolactone) and delivered to the cathode, thereby causing reduction of oxygen to generate water ($H_2O$). The migration of electrons via this process is used for power generation.

Biofuel cells are thought to hold promise as power generation devices for use in fields that are not suitable for conventional cells, such as wearable devices or single-use devices, since they have a simple cell structure, are operable at room temperature, are highly environmentally or biologically compatible, and materials are readily available.

For example, non-patent document 1 describes a power generation device that has electrodes printed on paper using a material including an enzyme that promotes oxidation of glucose. The device generates electricity by oxidation of glucose caused by supplying glucose to the anode by allowing the paper to absorb a liquid containing glucose.

PRIOR ART DOCUMENT

Patent Document

[Non-Patent Document 1] I. Shitanda et al., Chem. Comm. 2013

SUMMARY OF THE INVENTION

Problems to be Solved by the Invention

The power generation device described in non-patent document 1 is dry before use, and is suitable as a wearable device or a single-use device. However, the device is problematic in terms of securing a stable output depending on the concentration of fuel in the liquid to be supplied.

In view of the foregoing, the invention aims to provide a power generation device that exhibits excellent output stability, and to provide a power generation method and a concentration measurement method using the power generation device.

Means for Solving the Problem

The means for solving the problem includes the following embodiments.

<1> A power generation device, comprising a fuel, an anode and a cathode, the anode comprising an enzyme that promotes oxidation of the fuel, and the power generation device containing more water when generating power than when not generating power.

<2> A power generation device, comprising a fuel, an anode and a cathode, the anode comprising an enzyme that promotes oxidation of the fuel, and the power generation device generating power by supply of a liquid.

<3> A power generation device, comprising a fuel, an anode and a cathode, the anode comprising an enzyme that promotes oxidation of the fuel, and the power generation device containing water in an amount of 10% by mass or less relative to a total mass of the fuel, the anode and the cathode.

<4> The power generation device according to any one of <1> to <3>, wherein the fuel does not contain a solvent or contains a solvent in an amount of 50% by mass relative to the fuel.

<5> The power generation device according to any one of <1> to <4>, wherein the cathode comprises a catalyst that promotes reduction of oxygen.

<6> The power generation device according to any one of <1> to <5>, wherein the anode comprises an enzyme that promotes oxidation of a substance in a liquid that is supplied to the power generation device.

<7> The power generation device according to any one of <1> to <6>, comprising a layered body including a first substrate on which at least one of the anode or the cathode is formed and a second substrate that comprises the fuel.

<8> The power generation device according to any one of <1> to <7>, comprising a sheet or a rolled product of the sheet, the sheet comprising a plurality of the power generation devices formed on a substrate.

<9> The power generation device according to any one of <1> to <8>, which can be cut to a desired size for use.

<10> A power generation method, comprising supplying a liquid to the power generation device according to any one of <1> to <9>.

<11> The power generation method according to <10>, wherein the liquid comprises water.

<12> The power generation method according to <10> or <11>, wherein the liquid is supplied in an amount that imparts to the fuel, when mixed with the liquid, a concentration of from 0.01 $mol/dm^3$ to 10 $mol/dm^3$ at a use temperature.

<13> A concentration measurement method, comprising: supplying a liquid to the power generation device according to any one of <1> to <9>; and measuring a concentration of a substance included in the liquid.

Effect of the Invention

According to the invention, a power generation device that exhibits excellent output stability is provided. Further, a power generation method and a concentration measurement method using the power generation device are provided.

EMBODIMENTS FOR IMPLEMENTING THE INVENTION

Figure 1:
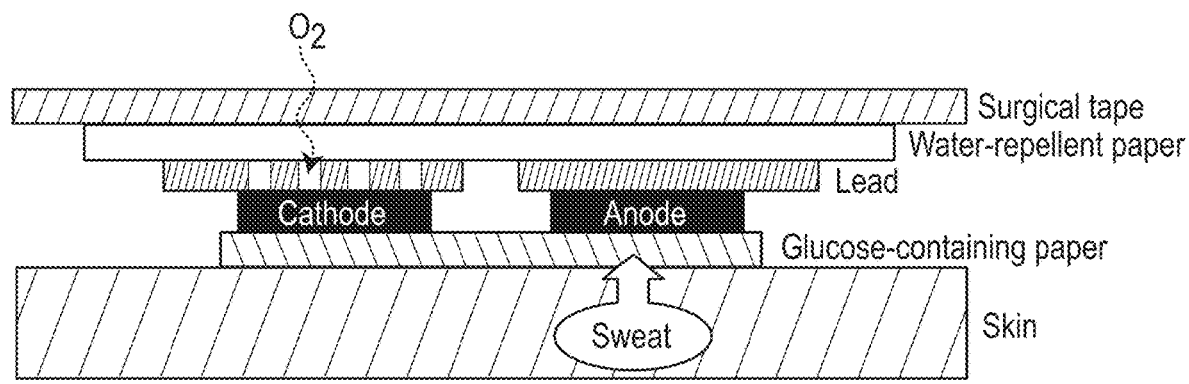
FIG. 1 is a schematic sectional view of an exemplary structure of a power generation device of the invention.

In the following, embodiments for implementing the invention are explained. However, the invention is not limited to these embodiments. The elements of the embodiments (including steps) are not essential, unless otherwise stated. The numbers and the ranges thereof do not limit the invention.

In the specification, numerical ranges represented by "from A to B" include A and B as a minimum value and a maximum value, respectively.

<Power Generation Device>

The first embodiment of the power generation device of the invention is a power generation device, comprising a fuel, an anode and a cathode, the anode comprising an enzyme that promotes oxidation of the fuel, and the power generation device containing more water when generating power than when not generating power.

The second embodiment of the power generation device of the invention is a power generation device, comprising a fuel, an anode and a cathode, the anode comprising an enzyme that promotes oxidation of the fuel, and the power generation device generating power by supply of a liquid.

The third embodiment of the power generation device of the invention is a power generation device, comprising a fuel, an anode and a cathode, the anode comprising an enzyme that promotes oxidation of the fuel, and the power generation device containing water in an amount of 10% by mass or less relative to a total mass of the fuel, the anode and the cathode (if the device includes a member such as a lead, a substrate or a spacer, the mass thereof is included therein).

The power generation device preliminarily includes a fuel for generating electricity. When the power generation device absorbs a liquid such as water, the fuel is mixed with the liquid and put into an oxidizable state by an enzyme included in the anode, whereby electricity is generated. Therefore, the power generation device exhibits excellent output stability without being largely affected by a concentration of the fuel in the liquid to be supplied. In addition, since the liquid may by either with or without a fuel included therein, expansion of the application of the power device can be anticipated.

Further, the power generation device of the invention satisfies at least one of (1) containing more water when generating power than when not generating power; (2) generating power by supply of a liquid; or (3) containing water in an amount of 10% by mass or less relative to a total mass of the fuel, the anode and the cathode.

Therefore, oxidation of the fuel does not occur when the device is not in use, and generation of electricity is suppressed.

From the viewpoint of suppressing oxidation of the fuel in a more reliable manner, the content of water in the power generation device is preferably 7% by mass or less relative to the total of the fuel, the anode and the cathode, more preferably 5% by mass or less relative to the total of the fuel, the anode and the cathode. Further, the content of water in each of the fuel, the anode and the cathode is preferably 10% by mass, respectively.

The content of water of the power generation device described herein refers to the content of water before the supply of a liquid to the power generation device.

(Fuel)

The fuel of the power generation device is not particularly limited as long as its oxidation is promoted by an enzyme. Examples of the fuel include sugars, alcohols, amino acids, amines, lactic acid and uric acid. The power generation device may include a single kind of fuel or two or more kinds thereof. The fuel may be a substance that directly becomes oxidizable by an enzyme included in the anode, or may be a substance that becomes oxidizable through hydrolysis or the like (for example, starch that becomes glucose by hydrolysis).

From the viewpoint of safety, biological affinity, output stability and handleability, when using the power generation device as a wearable device, a single-use device or the like, the fuel preferably includes a sugar. The type of the sugar includes monosaccharides, disaccharides, oligosaccharides and sugar alcohols.

As mentioned later, when the power generation device is used for a the purpose of measuring the concentration of a substance (object for the measurement) included in a liquid to be supplied, the fuel included in the power generation device is preferably a different substance from the object for the measurement.

The fuel may either with or without a solvent such as water or an organic solvent, but the fuel is preferably without a solvent. When the fuel includes a solvent, the content of the solvent is preferably 50% by mass or less relative to the total fuel, more preferably 30% by mass or less relative to the total fuel, further preferably 10% by mass or less relative to the total fuel.

The fuel may include an additive, such as a polymer, a filler or a fat. By including an additive, advantages in adjusting the amount of a liquid as supplied, promoting the dissolution of the fuel, and the like, are anticipated. Examples of the polymer include a water-absorbing polymer, a water-absorbing powder, and a water-soluble dietary fiber. Examples of the filler include pulp, microfibril cellulose (MFC) and biocellulose (BC).

The content of the fuel in the power generation device is not particularly limited, and may be determined depending on the application of the power generation device, and the like. From the viewpoint of achieving excellent output stability, the content of the fuel in the power generation device is preferably a content that imparts to the fuel, when mixed with a liquid to be supplied, a concentration of from 0.01 mol/dm$^3$ to 10 mol/dm$^3$, more preferably from 0.1 mol/dm$^3$ to 3 mol/dm$^3$, at a use temperature.

The position of the fuel in the power generation device is not particularly limited. For example, the fuel may be positioned adjacent to the anode, by including the fuel in a substrate that can absorb a liquid to be supplied to the power generation device. Alternatively, the fuel may be positioned inside the anode (for example, inside the pores of a porous anode).

When the fuel is included in a substrate, the method of including the fuel in the substrate is not particularly limited. For example, the fuel may be allowed to penetrate the substrate, or may be attached to a surface of the substrate.

Further, the fuel may be mixed with a material for a substrate, and formed into a sheet with the material.

The material for the substrate is not particularly limited, and may be either natural or artificial. From the viewpoint of environmental or biological affinity, the substrate is preferably a paper, a nonwoven fabric or a cloth, formed from a natural or biodegradable material. The thickness of the substrate is not particularly limited, and may be determined depending on the shape of the power generation device, and the like.

(Anode and Cathode)

The material for the anode and the cathode (hereinafter, also collectively referred to as an electrode) is not particularly limited, as long as it includes an electroconductive material.

Examples of the electroconductive material include a carbon material and a metal. From the viewpoint of disposability and biological affinity, a carbon material is preferred.

Examples of the carbon material include graphite, carbon black (such as Ketchen black and acetylene black), mesoporous carbon such as MgO-templated carbon obtained by a template method (preferably with a meso/micro pore size of from 10 nm to 150 nm and a particle size of from 0.5 μm to 10 μm). A single kind of the carbon material may be used, or two or more kinds may be used in combination.

The electrode may further include a binder. The type of the binder is not particularly limited, and examples thereof include a resin. Examples of the resin include polyvinylidene difluoride (PVDF), styrene-butadiene rubber (SBR), polytetrafluoroethylene (PTEE) and polyvinyl alcohol (PVA). A single kind of the binder may be used, or two or more kinds may be used in combination.

The type of the enzyme that promotes oxidation of the fuel is not particularly limited, and may be selected depending on the type of the fuel to be oxidized, or the like. A single kind of the enzyme may be included in the anode, or two or more kinds may be included in the anode. Further, the enzyme that promotes oxidation may be in combination with a catalyst, such as an enzyme that turns a fuel into an oxidizable state through hydrolysis or the like.

In a case of using a sugar as the fuel, examples of the enzyme includes glucose oxidase and glucose dehydrogenase, when the fuel is glucose; fructose oxidase or fructose dehydrogenase when the fuel is fructose; a combination of invertase and glucose dehydrogenase, when the fuel is sucrose; and a combination of amylase and glucose dehydrogenase, when the fuel is starch.

When the fuel is a substance other than a sugar, for example, lactate oxidaze may be used as an enzyme when the fuel is lactic acid.

In a case of using the power generation device for measuring a concentration of a substance (object to be measured) in a liquid to be supplied, the anode may further include an enzyme that promotes oxidation of the substance, in addition to an enzyme that promotes oxidation of the fuel. The substance as an object to be measured is not particularly limited, as long as its oxidation is promoted by an enzyme. In a case of measuring a concentration of a substance in a living body, examples of the substance include glucose, lactic acid and uric acid.

Exemplary structures of the power generation device, when including an enzyme that promotes oxidation of a substance as an object to be measured, include (1) a structure in which an enzyme that promotes oxidation of a fuel and an enzyme that promotes oxidation of the substance for the measurement are included in an anode of the same device; and (2) a structure in which an enzyme that promotes oxidation of a fuel and an enzyme that promotes oxidation of the substance for the measurement are included in different anodes, respectively, of different devices that are electrically connected with or without a wire.

From the viewpoint of clearly distinguishing the amount of power generation, which is derived from the fuel, from the amount of power generation, which is derived from the substance for the measurement, a structure described in (2) is preferred.

The cathode preferably includes a catalyst that promotes reduction of oxygen. The type of the catalyst is not particularly limited, and may be either an organic substance or an inorganic substance. From the viewpoint of disposability and biological affinity, an organic substance is preferred. Examples of the organic substance include an enzyme that promotes reduction of oxygen, such as bilirubin oxidase and laccase. Examples of the inorganic substance include a metallic catalyst such as platinum. The cathode may include a single kind of a catalyst or may include two or more kinds.

The position of the enzyme or the catalyst in the electrode is not particularly limited. From the viewpoint of efficiently gaining the ability to promote oxidation or reduction, the enzyme or the catalyst is preferably located at a surface of the electrode, at which the electrode contacts the fuel or the catalyst. Examples of a method of improving the efficiency of power generation by increasing the surface at which the electrode contacts the fuel or the catalyst include a method of forming an electrode having pores and positioning the enzyme or the catalyst inside the pores. From the viewpoint of forming an electrode having pores, a material in the form of particles is preferably used as an electroconductive material, more preferably a porous material in the form of particles. Examples of the porous material in the form of particles include mesoporous carbon prepared by a template method, such as MgO-templated carbon.

The position of the electrode in the power generation device is not particularly limited. From the viewpoint of reducing the thickness of the power generation device, the electrode is preferably formed on a substrate by applying a material for the electrode by screen printing or the like. In that case, the anode and the cathode may be formed on the same side of the substrate, or may be formed on different sides of the substrate, respectively.

A lead that electrically connects the electrodes may be formed on the substrate. The lead can be formed by using a common electrical material. The lead may have a through hole at a portion at which the substrate contacts the cathode, for the purpose of increasing the amount of oxygen to be supplied to the cathode.

The material for forming the substrate is not particularly limited, and may be either a natural material or an artificial material. From the viewpoint of environmental or biological affinity, the substrate is preferably a paper or a cloth formed from a natural material. From the viewpoint of avoiding short circuit between the anode and the cathode, which may be caused by a liquid to be supplied to the power generation device, a water-repellent product or a material that does not absorb the liquid may be used as a substrate. Alternatively, a spacer may be provided for avoiding short circuit caused between the anode and the cathode.

The form of the electrodes in the power generation device is not particularly limited. From the viewpoint of improving efficiency in power generation, the electrodes may be in a patterned form in which plural anodes and plural cathodes are connected.

(Other Members)

The power generation device may include a member other than the fuel and the electrodes, as necessary.

For example, the power generation device may include an adhesive that fixes the power generation device to an adherend, a protector that protect the power generation device from the outer environment, a hydrogel, and the like. In the specification, the "total of the fuel, the anode and the cathode", a basis for the calculation of the water content of the power generation device, refers to the total of the fuel, the anode, the cathode, and optionally the lead, the substrate and the spacer. Therefore, the mass of the other members, as mentioned above, is not included in the total mass as defined herein.

The power generation device may have instruments such as a tester for measuring the concentration of a substance in a liquid, which is supplied by using electricity generated by the electricity generated by the power generation device, or a wireless transmitter for transmitting the data obtained by the measurement. Since the power generation device preliminarily includes a fuel, it is possible to utilize the generated electricity for operating these instruments in a stable manner.

An exemplary embodiment of the power generation device, a sheet that is used by attaching the same to a skin, and a mechanism of generating electricity by absorption of sweat, are explained by referring to FIG. 1. However, the invention is not limited to the embodiment.

The power generation device shown in FIG. 1 includes an anode and a cathode that are formed on a sheet of water-repellent paper, as a substrate, via a lead, at a side that contacts a skin. A sheet of paper containing glucose, as a substrate containing a fuel, is positioned such that it contacts the anode and the cathode, and also contacts the skin. On the side of the water-repellent paper opposite to the anode and the cathode, there is a surgical tape for fixing the power generation device to the skin. The lead has through-holes for supplying oxygen ($O^2$) at a portion corresponding to the cathode.

When the power generation device shown in FIG. 1 is attached to a skin, sweat secreted from the skin is absorbed by the paper containing glucose. The glucose is mixed with the sweat and becomes oxidizable, thereby causing oxidation of glucose in the anode. Then, electrons generated by the oxidation of glucose migrate from the anode to the cathode, and cause reduction of oxygen supplied from an outer environment. Through this process, electricity is generated.

The power generation device may be in the form of individual pieces with a desired size for use, or may be cut into individual pieces of a desired size when using the same.

Figure 2:
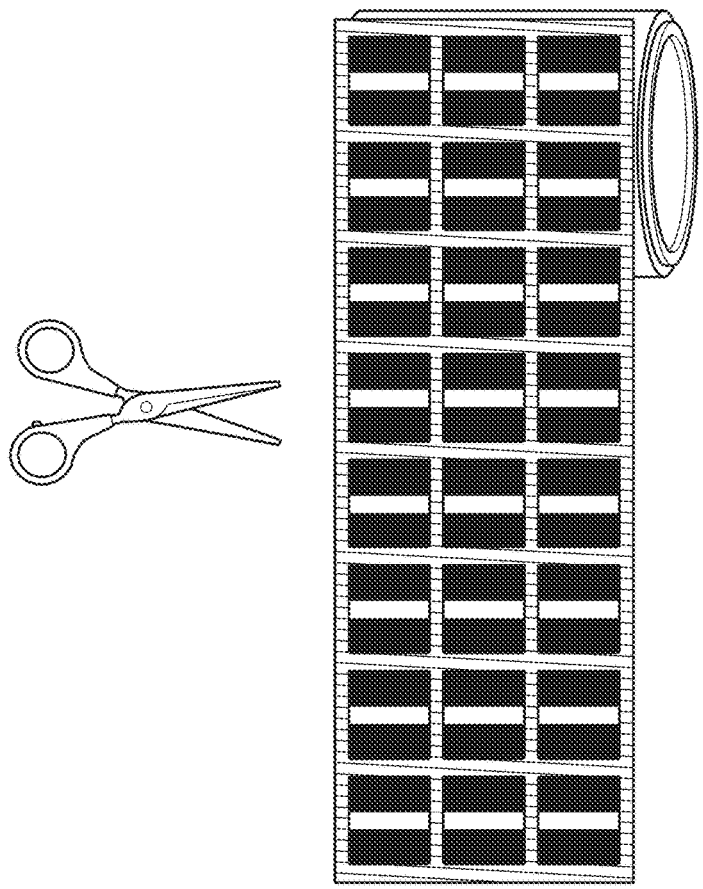
FIG. 2 is a schematic view of a rolled product of a sheet having plural power generation devices that are connected to each other and formed on a substrate.

For example, as shown in FIG. 2, the power generation device may be in the form of a sheet on which plural power generation devices are formed (the sheet may be in the form of a roll, as necessary) before use, and may be cut into a size in view of a desired degree of output to obtain. The power generation device may be in a layered form in which plural devices overlap each other in a thickness direction.

The thickness of the power generation device in the form of a sheet is not particularly limited, and may be determined depending on the application of the power generation device. For example, the thickness may be selected from 0.1 mm to 5 nm (excluding the thickness of the members as mentioned above).

Exemplary structures of the power generation device in the form of a sheet include a layered body including a first substrate on which at least one of the anode or the cathode is formed and a second substrate that includes the fuel.

The power generation device of the invention preferably used for various applications as a device that generates electricity when it is supplied with a liquid.

For example, since the power generation device can be used for a simple method for measuring a concentration of a substance in a living body, such as sweat, urine, eyewater or blood, it is suitably used for the purpose of health control or physical training control.

<Power Generation Method>

The power generation method of the invention includes supplying a liquid to the power generation device of the invention.

The liquid to be supplied is not particularly limited, as long as it causes oxidation of a fuel contained in the power generation device to generate electricity. Examples of the liquid include water and a mixture including water (such as a liquid obtained from a living body).

The amount of the liquid to be supplied is not particularly limited, as long as it is enough to cause the power generation device to generate electricity. For example, the liquid is preferably used in an amount that imparts to the fuel, when mixed with the liquid to be supplied, a concentration of from 0.01 mol/dm$^3$ to 10 mol/dm$^3$, more preferably from 0.1 mol/dm$^3$ to 3 mol/dm$^3$, at a use temperature.

<Concentration Measurement Method>

The concentration measurement method of the invention includes supplying a liquid to the power generation device of the invention; and measuring a concentration of a substance (object for the measurement) included in the liquid.

The concentration measurement method of the invention can be performed by using the power generation device in which the anode includes, in addition to an enzyme that promotes oxidation of the fuel, an enzyme that promotes oxidation of a substance to be measured. Details of the power generation device used in the concentration measurement method are as described above. The measurement of the concentration can be performed based on a degree or a change of the output of the power generation device, without particular restriction.

EXAMPLES

In the following, the invention is explained in more details by referring to the Examples. However, the invention is not limited to the Examples.

Example 1

(1) Formation of Electrode Pattern

A lead was formed on a substrate (Japanese paper IZUMO, Keynote Planning Co., Ltd.) that had been subjected to water-repellant treatment, by applying a carbon paste (JELCON CH-10, Jujo Chemical Co., Ltd.) by screen printing and drying the same at 120° C. for 30 minutes.

Figure 3:
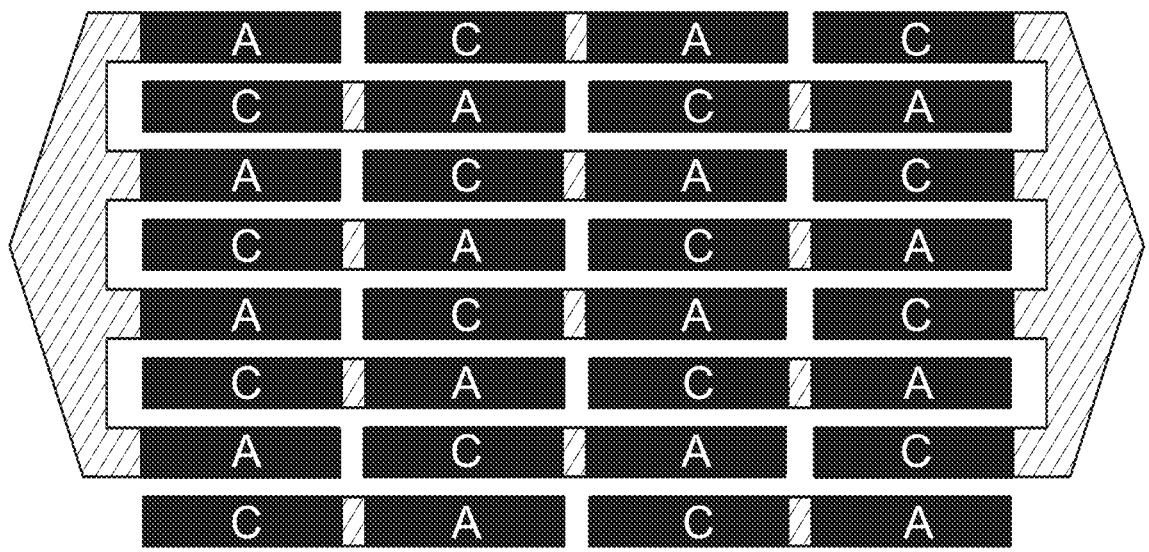
FIG. 3 is a planar view of a pattern of electrodes of a power generation device prepared in the Examples.

Subsequently, 440 mg of MgO-templated carbon (Toyo Tanso Co., Ltd.), 110 mg of polyvinylidene difluoride (Kureha Corporation) and 3 mL of isophorone (Fujifilm Wako Pure Chemical Corporation) were mixed to prepare a slurry-like electrode material. The electrode material was applied on the lead by screen printing to form 3 layers, dried at 45° C. for 30 minutes, thereby forming an electrode pattern including 16 anodes (20 mm×5 mm in each size) in which 4 anodes were arranged in series and 4 anodes were arranged in parallel. Then, the same electrode material was applied on the lead by screen printing to form 3 layers, dried at 45° C. for 30 minutes, thereby forming an electrode pattern including 16 cathodes (20 mm×5 mm in each size) in which 4 cathodes were arranged in series and 4 cathodes were arranged in parallel. FIG. 3 shows the electrode pattern formed by the anodes and the cathodes.

(2) Application of Enzyme

The electrode pattern was subjected to UV-O3 treatment for 15 minutes, and a saturated methanol solution of tetrathiafulvalene (Sigma-Aldrich) was dropped on a portion corresponding to the anode, as a mediator.

A liquid in which glucose oxidase (GOD, Fujifilm Wako Pure Chemical Corporation) was dispersed in a 1M phosphate buffer solution of pH 7.0 (10 unit/μL) was dropped on a portion corresponding to the anode (20 μL per anode).

A liquid in which bilirubin oxidase (BOD, Amano Enzyme Inc.) was dispersed in a 1M phosphate buffer solution of pH 7.0 (10 unit/μL), including 0.01% Triton-X (Roche Diagnostics GmbH, was dropped on a portion corresponding to the cathode (20 μL per cathode).

The substrate was dried for 1 hour under reduced pressure, thereby forming an anode including GOD as an enzyme that promotes oxidation of glucose and a cathode including BOD as an enzyme that promotes reduction of oxygen.

(3) Preparation of Power Generation Device

A 1M phosphate buffer solution including glucose of pH 7.0 (glucose concentration: 0.1 mol/dm$^3$) was dropped on a substrate (Japanese paper IZUMO, Keynote Planning Co., Ltd.) at an amount of 1 ml/cm$^2$, dried at 100° C. for 30 minutes, thereby preparing a substrate including glucose. A power generation device was prepared by positioning the substrate including glucose on the anode and the cathode as prepared above.

(4) Evaluation of Output

The output of the power generation device was evaluated by linear sweep voltammetry. The measurement was performed by a two-electrode method, at a scanning potential open-circuit voltage of 0V and a scanning rate of 1 mV/s. A liquid was supplied by dropping a 1M phosphate buffer solution of pH 7.0, at an amount of 1 ml/cm$^2$. A current-voltage curve obtained by the measurement is shown in FIG. 4.

For reference, a power generation device was prepared in the same manner to Example 1, except that a substrate without including glucose was placed on the anode and the cathode, instead of the substrate including glucose.

The output of the power generation device was evaluated in the same manner to Example 1, except that a liquid was supplied by dropping a 1M phosphate buffer solution of pH 7.0, including glucose at a concentration of 0.1 mol/dm$^3$, at an amount of 1 ml/cm$^2$. A current-voltage curve obtained by the measurement is shown in FIG. 4.

Figure 4:
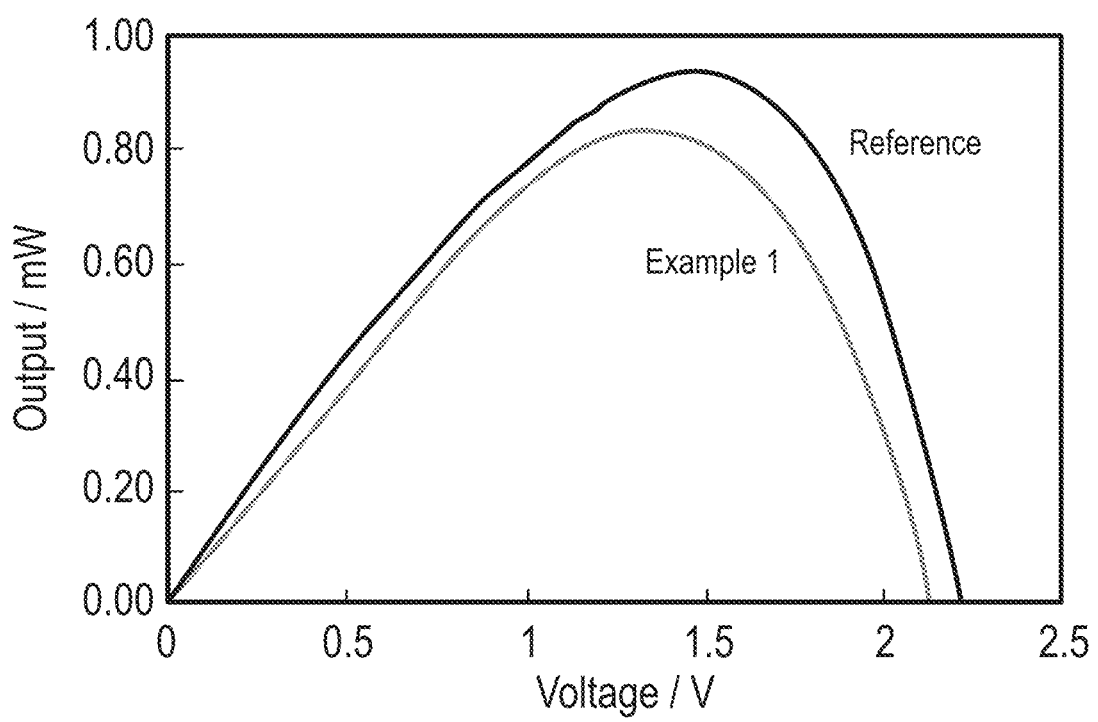
FIG. 4 is a graph showing the results of evaluating the degree of output of power generation devices prepared in the Examples.

As shown in FIG. 4, the power generation device prepared in Example 1 exhibited an open-circuit voltage of 2.13 A and a maximum output of 0.84 mW, which was approximately 89% of a maximum output obtained in the power generation device for reference (0.94 mW).

From these results, it is found that the power generation device exhibits an output equivalent to the output obtained by the power generation device for reference, a device to which a liquid including a fuel is supplied.

Further, it is suggested that the power generation device of the invention can achieve a stable output without considering whether or not a liquid to be supplied includes a fuel, or considering a concentration of a fuel in the liquid.

Example 2

(1) Formation of Electrode Pattern

A lead was formed on a substrate (Japanese paper IZUMO, Keynote Planning Co., Ltd.) that had been subjected to water-repellant treatment, by applying a carbon paste (JELCON CH-10, Jujo Chemical Co., Ltd.) by screen printing and drying the same at 120° C. for 30 minutes.

Subsequently, 1 g of MgO-templated carbon (Toyo Tanso Co., Ltd.), 5 mL of a polyvinylidene difluoride solution (Kureha Corporation) and 2.5 mL of n-methylpyrrolidone were mixed to prepare a slurry-like electrode material. The electrode material was applied on the lead by screen printing to form 3 layers, dried at 60° C. for 30 minutes, thereby forming the same electrode pattern as Example 1 formed by the anodes and the cathodes (20 mm×5 mm in each size).

(2) Application of Enzyme

The electrode pattern was subjected to UV-O3 treatment for 15 minutes, and a saturated solution of 1,2-naphthoquinone was dropped on a portion corresponding to the anode, as a mediator.

A liquid in which glucose dehydrogenase (GHD, Fujifilm Wako Pure Chemical Corporation) was dispersed in a 1M phosphate buffer solution of pH 7.0 was dropped on a portion corresponding to the anode at an amount of 400 U/cm$^2$.

A liquid in which bilirubin oxidase (BOD, Amano Enzyme Inc.) was dispersed in a 1M phosphate buffer solution of pH 7.0, including 0.01% Triton-X (Roche Diagnostics GmbH, was dropped on a portion corresponding to the cathode at an amount of 40 U/cm$^2$.

The substrate was dried for 1 hour under reduced pressure, thereby forming an anode including GHD as an enzyme that promotes oxidation of glucose and a cathode including BOD as an enzyme that promotes reduction of oxygen.

(3) Preparation of Power Generation Device

A 1M phosphate buffer solution including glucose of pH 7.0 was dropped on a substrate (Japanese paper IZUMO, Keynote Planning Co., Ltd.) at an amount of 1 mL/cm$^2$, dried at 100° C. for 1 hour, thereby preparing a substrate including glucose. Power generation devices were prepared by positioning the substrate including glucose on the anode and the cathode as prepared above, with a glucose concentration of the phosphate buffer solution of 0.005 mol/dm$^3$ (a), 0.01 mol/dm$^3$ (b), 0.015 mol/dm$^3$ (c) and 0.02 mol/dm$^3$ (d), respectively.

(4) Evaluation of Output

The output of the power generation devices was evaluated by linear sweep voltammetry. The measurement was performed by a two-electrode method, at a scanning potential open-circuit voltage of 0V and a scanning rate of 1 mV/s. A liquid was supplied by dropping ultrapure water at an amount of 1 mL/cm$^2$. A current-voltage curve obtained by the measurement is shown in FIG. 5.

Figure 5:
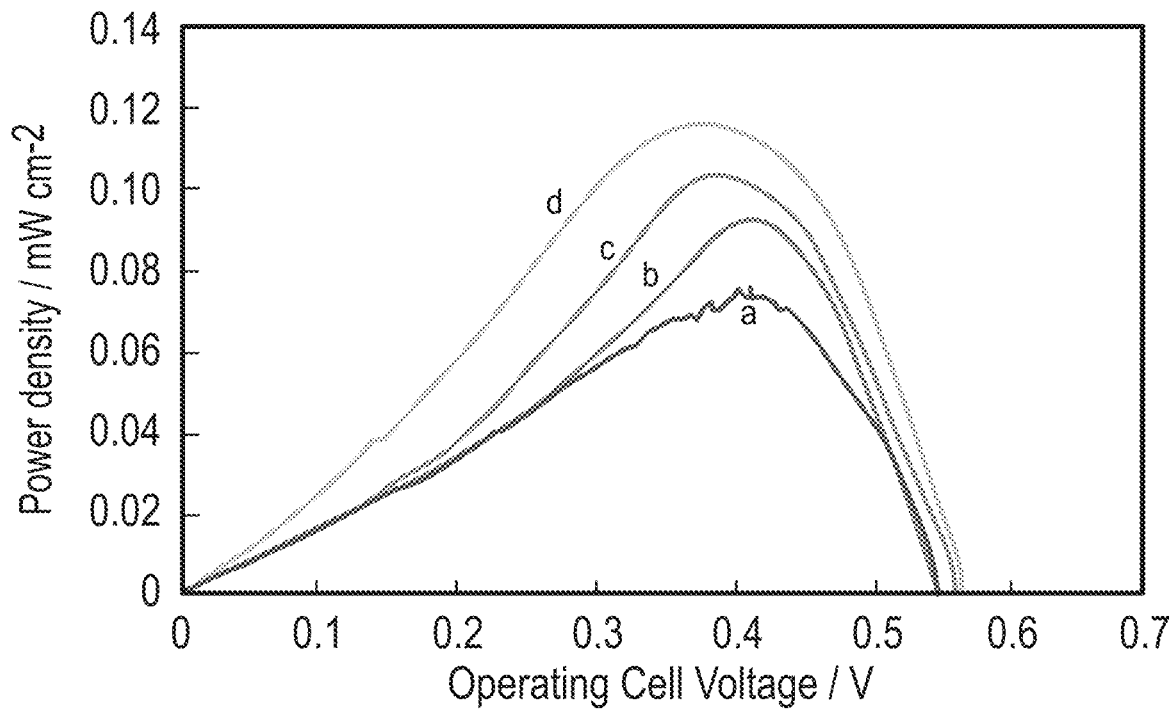
FIG. 5 is a graph showing the results of evaluating the degree of output of power generation devices prepared in the Examples.

As shown in FIG. 5, the power generation device prepared in Example 2 exhibited an open-circuit voltage of 0.57 V. The maximum output was 0.116 mW$^{-2}$ when the glucose concentration was 0.02 mol/dm$^3$ (20 mM). From these results, it is confirmed that electricity can be generated by supplying water to a power generation device that includes glucose as a fuel, and that the degree of output depends on the glucose concentration.

Example 3

Power generation devices were prepared in the same manner to Example 2, except that the anode was prepared by using lactate oxidase (product under development, LOx, 40 U/cm$^2$) instead of GDH, and that a 1M phosphate buffer solution of pH 7.0, including lactic acid instead of glucose, was used. The concentration of lactic acid in the phosphate buffer solution in the devices was 0 mol/dm$^3$ (a), 0.01 mol/dm$^3$ (b) and 0.1 mol/dm$^3$ (c), respectively. A current-voltage curve obtained by the measurement is shown in FIG. 6.

Figure 6:
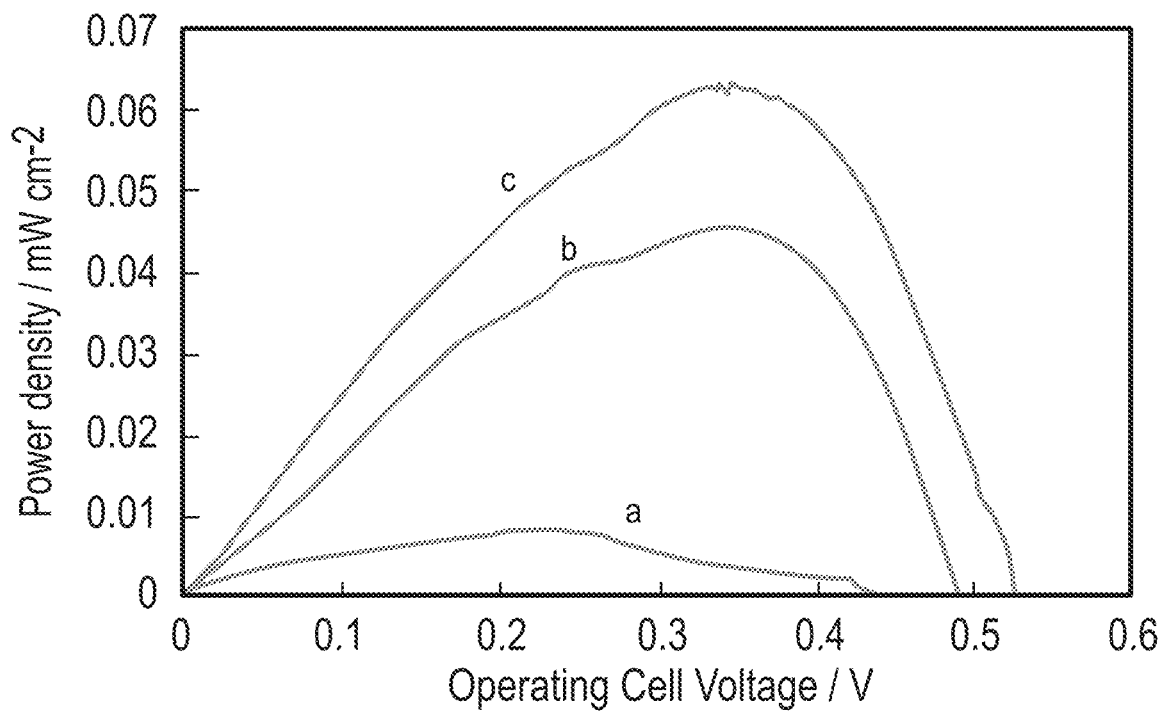
FIG. 6 is a graph showing the results of evaluating the degree of output of the power generation devices prepared in the Examples.

As shown in FIG. 6, the power generation device prepared in Example 3 exhibited an open-circuit voltage of 0.50 V. The maximum output was 0.065 mW-2 when the glucose concentration was 0.1 mol/dm$^3$ (100 mM). From these results, it is confirmed that electricity can be generated by supplying water to a power generation device that includes lactic acid as a fuel, and that the degree of output depends on the lactic acid concentration.

<Exemplary Applications>

Figure 7:
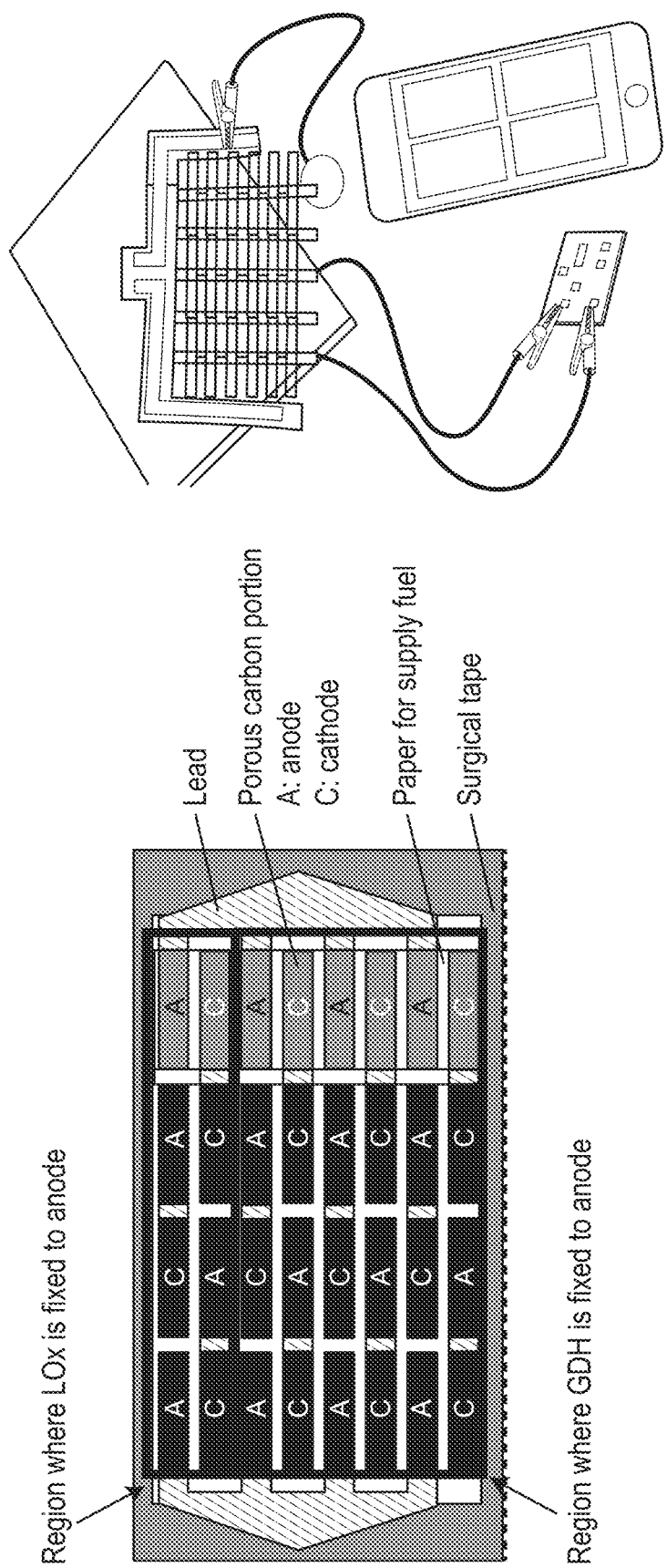
FIG. 7 is a view showing an exemplary configuration of a wearable device to which a power generation device is applied.

From the results of the Examples, it is found that a sufficient output can be obtained, even if the fuel is a substance other than glucose, by combining a suitable enzyme for promoting oxidation of the fuel. By utilizing this property, it is thought that a wearable device having a structure shown in FIG. 7 can be prepared. The wearable device shown in FIG. 7 has an anode including an enzyme that promotes oxidation of glucose (GOD or GDH) and an anode including an enzyme that promotes oxidation of lactic acid (LOx). When the device is combined with a substrate including glucose, for example, glucose is allowed to elute by sweat supplied from a skin to which the device is attached. By utilizing this as a driving force, a current detector (capable of wireless transmission) is driven to monitor the amount of lactic acid in the sweat based on the data of the current value. Therefore, for example, the device makes it possible to evaluate a degree of fatigue of a person wearing the device, based on the amount of lactic acid.

The invention claimed is:

1. A power generation device, comprising a fuel, an anode, a cathode, a first substrate made of paper formed from a natural or biodegradable material, and a second substrate having water repellency or that does not absorb a liquid supplied to the power generation device,
the fuel penetrating the first substrate, being absorbed by the first substrate, or being mixed with a material for the first substrate and being formed into a sheet with the material to form the first substrate,
the anode comprising an enzyme that promotes oxidation of the fuel,
the fuel being positioned between the anode and the cathode,
the anode and the cathode being in contact with the first substrate and positioned between the first substrate and the second substrate, and
the power generation device containing water in an amount of 10% by mass or less relative to a total mass of the fuel, the anode, and the cathode,
wherein the power generation device does not contain a liquid obtained from a living body.

2. A power generation device, comprising a fuel, an anode, a cathode, a first substrate made of paper formed from a natural or biodegradable material, and a second substrate having water repellency or that does not absorb a liquid supplied to the power generation device,
the fuel penetrating the first substrate, being absorbed by the first substrate, or being mixed with a material for the first substrate and being formed into a sheet with the material to form the first substrate,
the anode comprising an enzyme that promotes oxidation of the fuel,
the anode and the cathode being positioned on the same side of the first substrate, such that the anode and the cathode contact the first substrate,
the anode and the cathode being in contact with the first substrate and positioned between the first substrate and the second substrate, and
the power generation device containing water in an amount of 10% by mass or less relative to a total mass of the fuel, the anode, and the cathode,
wherein the power generation device does not contain a liquid obtained from a living body.

3. A power generation device, comprising a fuel, an anode, a cathode, a first substrate made of paper formed from a natural or biodegradable material, and a second substrate having water repellency or that does not absorb a liquid supplied to the power generation device,
the fuel penetrating the first substrate, being absorbed by the first substrate, or being mixed with a material for the first substrate and being formed into a sheet with the material to form the first substrate,
the anode comprising an enzyme that promotes oxidation of the fuel,
an enzyme that promotes oxidation of a substance included in a liquid to be supplied to the power generation device,
the anode and the cathode being in contact with the first substrate and positioned between the first substrate and the second substrate, and
the power generation device containing water in an amount of 10% by mass or less relative to a total mass of the fuel, the anode, and the cathode,
wherein the power generation device does not contain a liquid obtained from a living body.

4. The power generation device according to claim 1, wherein the fuel does not contain a solvent or contains a solvent in an amount of 50% by mass relative to the fuel.

5. The power generation device according to claim 1, wherein the cathode comprises a catalyst that promotes reduction of oxygen.

6. The power generation device according to claim 1, wherein the fuel comprises a monosaccharide.

7. The power generation device according to claim 1, comprising a sheet or a rolled product of the sheet, the sheet comprising a plurality of the power generation devices formed on the first substrate.

8. The power generation device according to claim 1, which can be cut to a desired size for use.

9. A power generation method, comprising supplying a liquid to the power generation device according to claim 1.

10. The power generation method according to claim 9, wherein the liquid comprises water.

11. The power generation method according to claim 9, wherein the liquid is supplied in an amount that imparts to the fuel, when mixed with the liquid, a concentration of from 0.01 mol/dm$^3$ to 10 mol/dm$^3$ at a use temperature.

12. A concentration measurement method, comprising:
supplying a liquid to the power generation device according to claim 1; and
measuring a concentration of a substance included in the liquid.

13. A concentration measurement method, comprising:
supplying a liquid to a power generation device, and
measuring a concentration of a substance included in the liquid,
the power generation device comprising a fuel, an anode, a cathode, a first substrate made of paper formed from a natural or biodegradable material, and a second substrate having water repellency or that does not absorb a liquid supplied to the power generation device, the fuel penetrating the first substrate, being absorbed by the first substrate, or being mixed with a material for the first substrate and being formed into a sheet with the material to form the first substrate,
the anode comprising an enzyme that promotes oxidation of the fuel,
the anode and the cathode being in contact with the first substrate and positioned between the first substrate and the second substrate, and
the power generation device containing water in an amount of 10% by mass or less relative to a total mass of the fuel, the anode, and the cathode,
wherein the power generation device does not contain a liquid obtained from a living body.

14. The power generation device according to claim 2, wherein the fuel does not contain a solvent or contains a solvent in an amount of 50% by mass relative to the fuel.

15. The power generation device according to claim 2, wherein the cathode comprises a catalyst that promotes reduction of oxygen.

16. The power generation device according to claim 2, wherein the fuel comprises a monosaccharide.

17. The power generation device according to claim 2, comprising a sheet or a rolled product of the sheet, the sheet comprising a plurality of the power generation devices formed on the first substrate.

18. A power generation method, comprising supplying a liquid to a power generation device comprising an oxidizable fuel in a non-oxidized state prior to supplying the liquid to the device, an anode, a cathode, a first substrate made of paper formed from a natural or biodegradable material, the fuel penetrating the first substrate, being absorbed by the first substrate, or being mixed with a material for the first substrate and being formed into a sheet with the material to form the first substrate, and a second substrate having water repellency or that does not absorb a liquid supplied to the power generation device,
the anode comprising an enzyme that promotes oxidation of the fuel,
the first substrate including the fuel being positioned between the anode and the cathode,
the anode and the cathode being in contact with the first substrate and positioned between the first substrate and the second substrate, and
the power generation device generating power by supply of a sufficient quantity of the liquid to allow oxidation of the fuel by the enzyme contained in the device, and
the power generation device containing water in an amount of 10% by mass or less relative to a total mass of the fuel, the anode, and the cathode,
wherein the power generation device does not contain a liquid obtained from a living body.

19. The power generation device of claim 1, wherein the second substrate is formed of paper.

20. The power generation device of claim 2, wherein the second substrate is formed of paper.

21. The power generation device of claim 3, wherein the second substrate is formed of paper.

22. The power generation method of claim 9, wherein the second substrate is formed of paper.

23. The concentration measurement method of claim 13, wherein the second substrate is formed of paper.

24. The power generation method of claim 18, wherein the second substrate is formed of paper.

25. The power generation method of claim 9, wherein the first substrate is in direct contact with a skin to which the power generation device is attached.

26. The concentration measurement method of claim 12, wherein the first substrate is in direct contact with a skin to which the power generation device is attached.

27. The concentration measurement method of claim 13, wherein the first substrate is in direct contact with a skin to which the power generation device is attached.

28. The power generation method of claim 18, wherein the first substrate is in direct contact with a skin to which the power generation device is attached.

* * * * *